Figure 1:
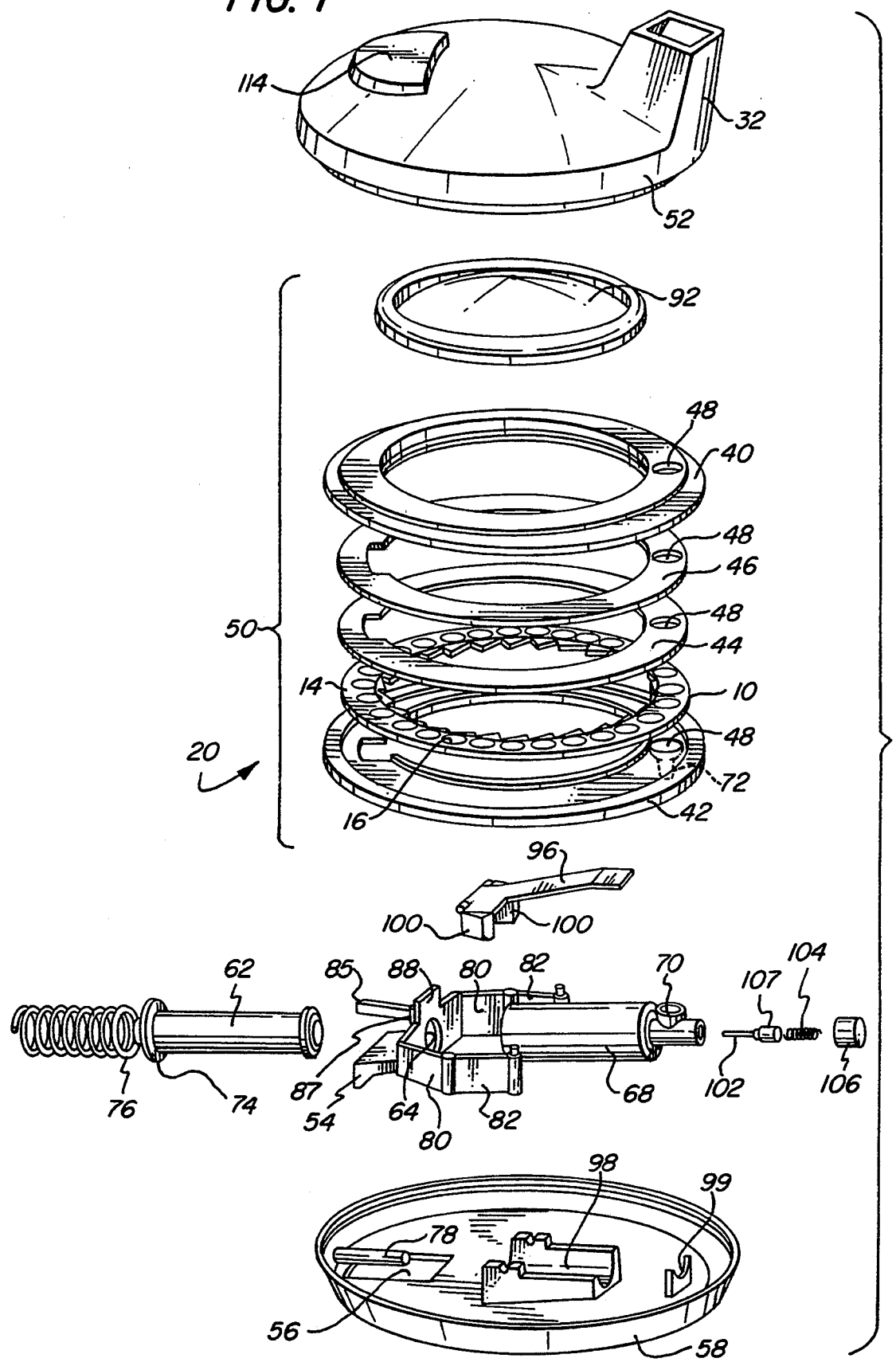

United States Patent [19]
Mulhauser et al.

[11] Patent Number: 5,388,572
[45] Date of Patent: Feb. 14, 1995

[54] DRY POWDER MEDICAMENT INHALATOR HAVING AN INHALATION-ACTIVATED PISTON TO AEROSOLIZE DOSE AND DELIVER SAME

[75] Inventors: Paul Mulhauser, New York; Jeffrey Karg, Waldwick; Thomas Foxen, Brooklyn; Christopher J. Brooks, Glen Head, all of N.Y.

[73] Assignee: Tenax Corporation (a Connecticut Corp.), Danbury, Conn.

[21] Appl. No.: 143,182

[22] Filed: Oct. 26, 1993

[51] Int. Cl.$^6$ .................. A61M 15/00; A61M 16/00; B05D 7/14; B05D 83/06
[52] U.S. Cl. .......................... 128/203.15; 128/204.13
[58] Field of Search ................ 128/203.15, 203.21, 128/200.22, 200.21, 204.13; 604/52; 206/528

[56] References Cited

U.S. PATENT DOCUMENTS

| | | | |
|---|---|---|---|
| 2,470,298 | 5/1949 | Fields | 128/272 |
| 2,503,732 | 4/1950 | Heisterkamp | 128/207 |
| 2,517,482 | 8/1950 | Hall | 128/206 |
| 2,549,303 | 4/1951 | Friden | 128/206 |
| 2,569,720 | 10/1951 | Jesnig | 128/206 |
| 2,573,918 | 11/1951 | McCuiston | 128/206 |
| 2,579,280 | 12/1951 | Trumbour | 128/206 |
| 2,581,182 | 1/1952 | Fields | 128/206 |

(List continued on next page.)

FOREIGN PATENT DOCUMENTS

| | | |
|---|---|---|
| 0211595A2 | 2/1987 | European Pat. Off. . |
| 0166294B1 | 10/1989 | European Pat. Off. . |
| 0407028A2 | 1/1991 | European Pat. Off. . |
| 0424790A2 | 5/1991 | European Pat. Off. . |
| 0428380A1 | 5/1991 | European Pat. Off. . |
| 0451745A1 | 10/1991 | European Pat. Off. . |
| 0455463A1 | 11/1991 | European Pat. Off. . |
| 0467172A1 | 1/1992 | European Pat. Off. . |
| 2837040 | 2/1980 | Germany . |
| 3607187A1 | 9/1987 | Germany . |
| 4020571A1 | 6/1990 | Germany . |
| 4004904A1 | 9/1990 | Germany . |
| 4133274A1 | 2/1993 | Germany . |
| 2144997A | 3/1985 | United Kingdom . |
| 2246299A | 1/1992 | United Kingdom . |
| 1692470A1 | 11/1991 | U.S.S.R. . |
| WO90/13328 | 11/1990 | WIPO . |
| WO91/02558 | 3/1991 | WIPO . |
| WO91/02597 | 3/1991 | WIPO . |
| WO91/06334 | 5/1991 | WIPO . |
| WO91/13646 | 9/1991 | WIPO . |
| WO91/17784 | 11/1991 | WIPO . |
| WO91/19524 | 12/1991 | WIPO . |
| WO92/00115 | 1/1992 | WIPO . |
| WO92/04066 | 3/1992 | WIPO . |
| WO92/04067 | 3/1992 | WIPO . |
| WO92/04068 | 3/1992 | WIPO . |
| WO92/04069 | 3/1992 | WIPO . |
| WO93/12831 | 7/1993 | WIPO . |

*Primary Examiner*—Kimberly L. Asher
*Attorney, Agent, or Firm*—Kramer, Brufsky & Cifelli

[57] ABSTRACT

A dry powder inhalator for delivering a precise dose of a medicament contains a mesh disc impregnated with a series of spaced, medicament doses about the disc periphery. The inhalator is armed by manually retracting a finger pull extending downwardly from the bottom of the inhalator housing or rotating the bottom of the housing. The user inserts a mouthpiece on the housing into the mouth and inhales. This causes a chamber in the housing under a diaphragm to evacuate, thereby pulling the diaphragm down onto a knock out lever. The pivoting of the lever enables release of a piston into a cylinder which first compresses, and then dispenses a reduced volume of air at high pressure in a burst up through the medicament disc. When the burst of air hits the impregnated disc, the dose is forced out of the mesh's interstices, producing a cloud of the drug in its powdered form, which is inhaled by the user.

10 Claims, 15 Drawing Sheets

U.S. PATENT DOCUMENTS

| | | | |
|---|---|---|---|
| 2,592,369 | 4/1952 | Young | 128/206 |
| 2,603,215 | 7/1952 | Arnow | 128/206 |
| 2,603,216 | 7/1952 | Taplin | 128/206 |
| 2,604,094 | 7/1952 | Miller | 128/206 |
| 2,672,865 | 3/1954 | Willis | 128/206 |
| 2,722,935 | 11/1955 | Thompson | 128/266 |
| 2,946,332 | 7/1960 | Sacks | 128/266 |
| 2,992,645 | 7/1961 | Fowler | 128/208 |
| 3,518,992 | 7/1970 | Altounyan | 128/208 |
| 3,669,113 | 6/1972 | Altounyan | 128/266 |
| 3,795,244 | 3/1974 | Lax | 128/266 |
| 3,807,400 | 4/1974 | Cocozza | 128/266 |
| 3,809,084 | 5/1974 | Hansen | 128/266 |
| 3,837,341 | 9/1974 | Bell | 128/266 |
| 3,858,583 | 1/1975 | Hallworth | 128/266 |
| 3,870,046 | 3/1975 | Elliott | 128/266 |
| 3,888,253 | 6/1975 | Watt | 128/266 |
| 3,897,779 | 8/1975 | Hansen | 128/266 |
| 3,906,950 | 9/1975 | Cocozza | 128/206 |
| 3,921,637 | 11/1975 | Bennie | 128/266 |
| 3,948,264 | 4/1976 | Wilke | 128/266 |
| 3,949,751 | 4/1976 | Birch | 128/266 |
| 3,964,483 | 6/1976 | Mathes | 128/266 |
| 3,971,377 | 7/1976 | Damani | 128/266 |
| 3,973,566 | 8/1976 | Mathes | 128/266 |
| 3,980,074 | 9/1976 | Watt | 128/2 A |
| 3,991,761 | 11/1976 | Cocozza | 128/266 |
| 4,013,075 | 3/1977 | Cocozza | 128/266 |
| 4,014,336 | 3/1977 | Mathes | 128/266 |
| 4,047,525 | 9/1977 | Kulessa | 128/208 |
| 4,064,878 | 12/1977 | Lundquist | 128/206 |
| 4,069,819 | 1/1978 | Valentini | 128/206 |
| 4,098,273 | 7/1978 | Glenn | 128/206 |
| 4,105,027 | 8/1978 | Lundquist | 128/206 |
| 4,116,195 | 9/1978 | James | 128/266 |
| 4,117,844 | 10/1978 | James | 128/266 |
| 4,147,166 | 4/1979 | Hansen | 128/266 |
| 4,192,309 | 3/1980 | Poulsen | 128/203.15 |
| 4,200,099 | 4/1980 | Guenzel | 128/266 |
| 4,206,758 | 6/1980 | Hallworth | 128/203.15 |
| 4,227,522 | 10/1980 | Carris | 128/203.15 |
| 4,249,526 | 2/1981 | Dean | 128/203.15 |
| 4,307,734 | 12/1981 | Blankenship | 131/329 |
| 4,338,931 | 7/1982 | Cavazza | 128/203.15 |
| 4,353,365 | 10/1982 | Hallworth | 128/203.15 |
| 4,371,101 | 2/1983 | Cane | 222/636 |
| 4,423,724 | 1/1984 | Young | 128/203.15 |
| 4,446,862 | 5/1984 | Baum | 128/203.15 |
| 4,534,345 | 8/1985 | Wetterlin | 128/203.15 |
| 4,570,630 | 2/1986 | Elliott | 128/203.15 |
| 4,620,847 | 11/1986 | Shishov | 604/58 |
| 4,627,432 | 12/1986 | Newell | 128/203.15 |
| 4,662,915 | 5/1987 | Shirai | 55/511 |
| 4,667,668 | 5/1987 | Wetterlin | 128/203.15 |
| 4,668,218 | 5/1987 | Virtanen | 604/58 |
| 4,709,837 | 12/1987 | Erdman | 222/636 |
| 4,739,754 | 4/1988 | Shaner | 128/203.15 |
| 4,805,811 | 2/1989 | Wetterlin | 222/337 |
| 4,811,731 | 3/1989 | Newell | 128/203.15 |
| 4,841,964 | 6/1989 | Hurka | 128/203.15 |
| 4,846,168 | 7/1989 | Abiko | 128/203.15 |
| 4,884,565 | 12/1989 | Cocozza | 128/203.21 |
| 4,889,114 | 12/1989 | Kladders | 128/203.15 |
| 4,907,583 | 3/1990 | Wetterlin | 128/203.15 |
| 5,239,992 | 8/1993 | Bougamont et al. | 128/203.12 |

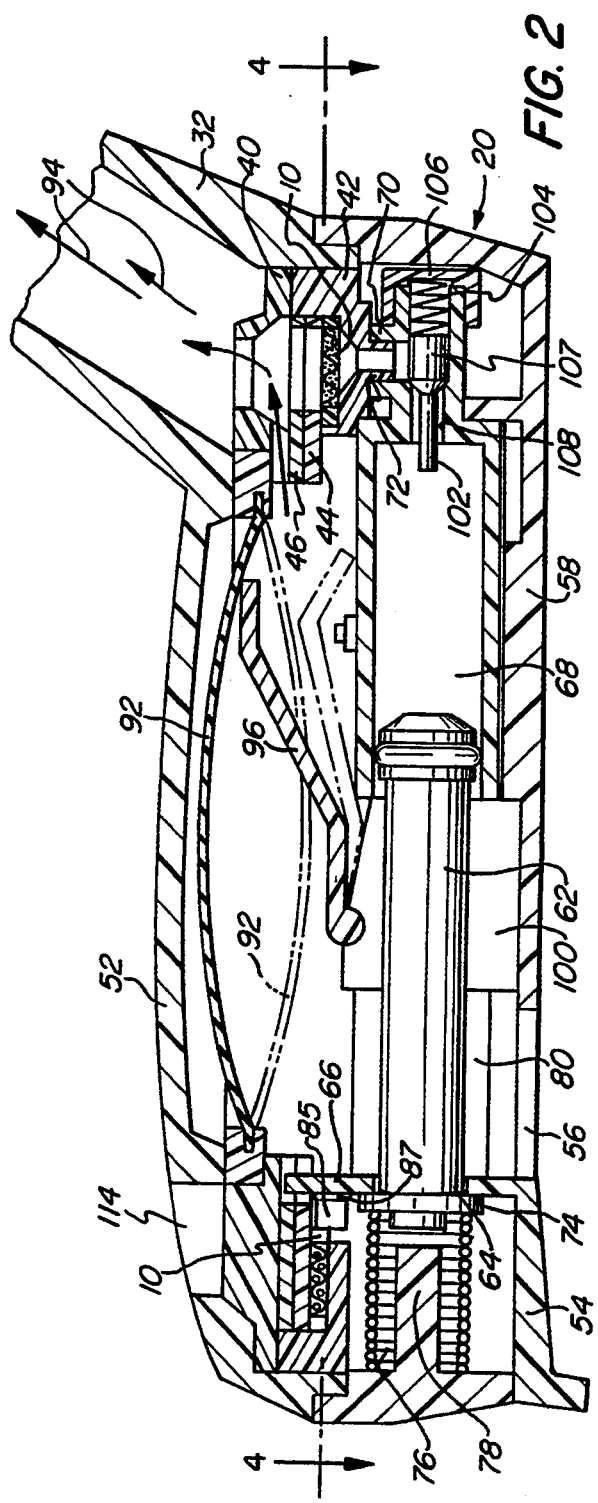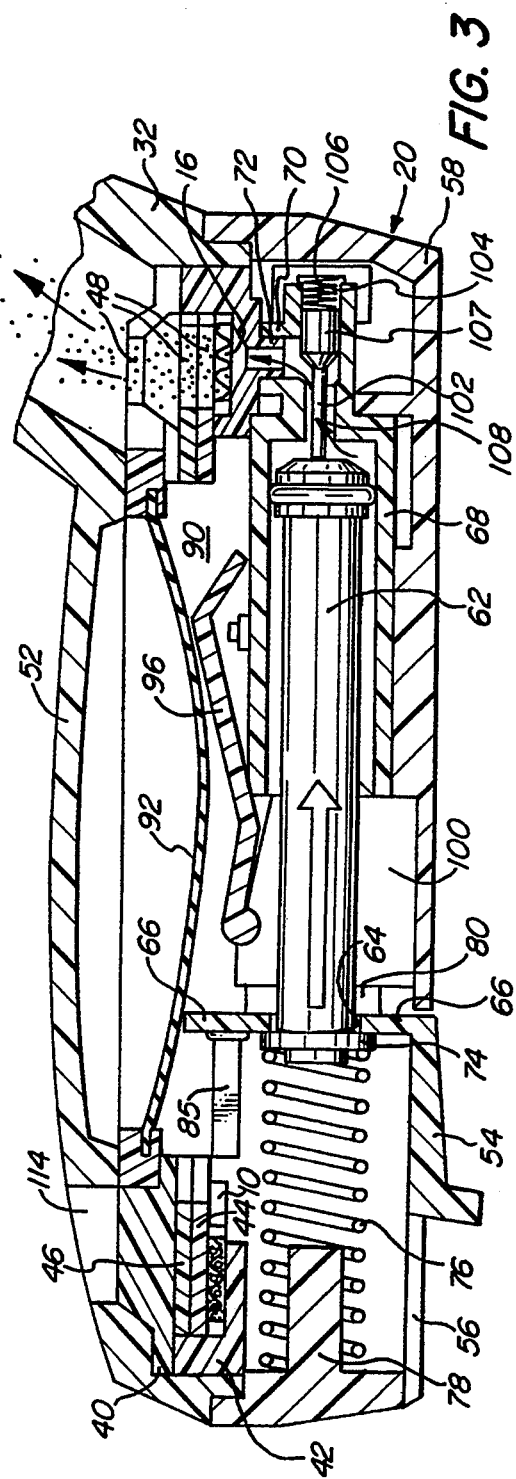

DRY POWDER MEDICAMENT INHALATOR HAVING AN INHALATION-ACTIVATED PISTON TO AEROSOLIZE DOSE AND DELIVER SAME

BACKGROUND OF THE INVENTION

1. Field of the Invention

This invention relates to a medicament inhalator, and more particularly, to a dry powder medicament inhalator usable by asthmatics and the like. By inhaling on a mouthpiece, a prescribed dosage of the medicament compressed within a disc housed within the inhalator is entrained in an air stream and inhaled by the user through the mouthpiece to coat the lungs of the user.

2. Description of the Prior Art

Asthma and other respiratory diseases have long been treated by the inhalation of an appropriate medicament to coat the bronchial tubes in the lungs to ease breathing and increase air capacity. For many years the two most widely used and convenient choices of treatment have been the inhalation of a medicament from a drug solution or suspension in a metered dose aerosol, pressurized inhalator, or inhalation of a powdered drug generally admixed with an excipient, from a dry powder inhalator. With growing concern being voiced over the strong link between depletion of the earth's atmospheric ozone layer and chlorofluorocarbon emissions, use of these materials in pressurized inhalators is being questioned, while an interest in dry powder inhalation systems has accordingly been stimulated.

Small quantities of a fine particle, preferably micronized powder, are used mainly for therapeutic purposes in treating diseases of the respiratory tract. Powders of this type, such as salmeterol hydronapthoate, in quantities generally below 50 micrograms (mg) are added to the respiratory air of the lung of the patient. It has been found that the particles of active materials should have a particle size of less than 5 microns ($\mu$) in thickness to insure that they penetrate deep into the lung. Thus, the metered dose must be atomized, aerosolized, or sufficiently broken up for inhalation by the patient to achieve the desired effect in the required dosage.

Presently, there are four different principal methods in use to provide fine particle powders without the use of propellants in the treatment of diseases of the respiratory tract.

The first method relies on the use of hard gelatin capsules which contain both a dose of the active material, and, in addition, potential adjuvants. The inhalator used by the asthmatic patient comprises a device for perforating or opening the capsule which is inserted into the inhalator when required. An air stream generated by a vacuum created by sucking action by the patient on a mouthpiece of the inhalator removes the powder contained within the opened capsule. The empty capsule is then expelled from the inhalator, which is then ready to receive the next capsule. Inhalators using this capsule-perforating technology or capsule-opening technology are shown in U.S. Pat. Nos. 3,906,950; 4,013,075; 3,807,400; and 3,991,761. In these inhalators, the capsule, when perforated, has both its ends held still during inhalation. The air stream which passes through it as a result of inhalation removes the powdered medicaments and is intended to remove all of the powdered medicament from the interior of the opened or broken capsule. However, it has been found that the air stream induced by the user-patient is generally insufficient in duration to remove the entire contents from the capsule which acts as a housing and in fact, impedes the removal of the medicament.

A further type of inhalator does not use individual capsules but instead is loaded with a package having a series of blisters equidistant from each other adjacent to its periphery. Each blister contains a fixed quantity of powdered medicament. As shown in EPO patent application publications EPO 211595 and 455463 along with EPO 467172 A1, when each blister is moved into a predetermined position, the blister is broken by a suitable opening device releasing the powder, which is then inhaled by the patient. It has been found that small water droplets of moisture contained within the depressions in the blister pack may cause agglomeration of the prepared medicament. Accordingly, when entrained in the air stream and inhaled by the user, the preferred particle size which can do the most good may not be readily achieved.

Another type of inhalator uses a container housing a quantity of medicament sufficient for several doses and is commonly known as the Draco Turbuhaler and is described in detail in U.S. Pat. Nos. 4,668,218, 4,667,668 and 4,805,811. The container includes a device for withdrawing the powdered medicament from the container and for preparing a dose for inhalation. The withdrawal and dose preparation includes a plate having a predetermined thickness and a certain number of cup-shaped or frusto-conical through holes. The plate can be moved by mechanical means from a position where a proportion of the holes are filled with powdered medicament taken from the container to another position in which the holes filled with medicament are located within a channel. Air flows into the channel as a result of suction provided by the patient on a mouthpiece in communication with the channel, to remove the powdered medicament from the holes. A scraper device is provided to level the powder in the plate holes and insures complete filling of the holes and consequently a constant dose. It has been found however that when suction is applied to entrain the medicament from one or more holes in the plate, not all the medicament is entrained but due to insufficient breathing capacity of the user and the non-cylindrical shape of the holes, some falls back into or never leaves the holes. Additionally, there is an agglomeration problem as mentioned previously. Accordingly, a vortex device has to be provided to aerosolize or atomize the agglomerated entrained medicament, even assuming the proper dosage leaves the holes in the rotated plate or disc.

The mechanical means for moving and indexing the perforated plate in the Draco Turbuhaler includes a rotatable knob fixed to the plate. Therefore, it is possible to present a double charge for inhalation as there is no indication of a charged state during use of the device. There is also the inherent waste of material in using a reservoir-type filling mechanism, which is never completely emptied and the device is gravity sensitive in that it must be maintained in a vertical, upright condition between uses because if inverted, most of the powder in the disc-sized holes will fall out, and be returned to the reservoir. Reindexing the device to fill the holes or perforations in the plate raises the possibility of overdosing the patient or losing count of a non-administered dose.

Another mechanical delivery system for a blister-type dry powder inhalator is shown in PCT application WO 93/12831. Air under pressure is driven by a piston continuously through a cylinder to impinge upon a microsized dose of medicament encapsulated on the periphery of a carrier disc. The air entrains the dry powdered medicament which is inhaled by a user. A similar delivery system is illustrated in German patent DE 4133274 A1 wherein a spring-driven piston delivers air into a chamber wherein it is admixed with dry powder medicament housed in the chamber and inhaled through a mouthpiece. But, in each of these systems, the air is continuously dispersed and dispensed through the powder in a steady stream, but not in a concentrated burst, thus substantially reducing its driving force along the outer reaches of the air stream, and subjecting the delivery of a full dose in part to the limited breathing capacity of the user or inhaler.

Finally, a process for supplying a medicament in a dry powder inhalator is disclosed in German Patent No. DE 4020571 A1 in which in manufacturing the aerosol, a velour or velvet-like material loaded with powder is introduced into a jet stream of air. The jet stream of air lifts the powder from the velour-like material by the Bernoulli effect, entrains the same, which is then inhaled by the user. The problem with this type of an arrangement is that the fibers themselves intermix with the medicament.

The present invention avoids many of the problems associated with the prior art, enabling a predetermined exact dose to be supplied through an inhalator with the ingested particle size of the powdered dose being formed for maximum beneficial efficiency.

SUMMARY OF THE INVENTION

In accordance with the present invention, the inhalator of the present invention utilizes a woven or nonwoven screen mesh disc impregnated at spaced locations along its circumference with a dose of powdered medicament, such as salmeterol hydronapthoate, which is useful in the treatment of asthma. The disc is selectively indexed so as to present the impregnated doses of medicament seriatim between a pair of holes in an upper and lower pressure plate in the inhalator. Air is forced through the holes in the pressure plates and the encapsulated screen mesh to entrain a dose of the powdered medicament, which is then inhaled through a mouthpiece, by the patient-user.

Because the powdered medicament is impregnated into the screen mesh, which could be woven, such as a silkscreen, or formed from polyamide fibers, or even stamped or etched from a piece of metal or ceramic, the air impinging upon the mesh and the powdered medicament will cause the medicament to break up as it is pressed up against and passed through the mesh infrastructure to aerosol or atomize the same so that the medicament is presented in appropriate particle sizes for maximum benefit when inhaled. Further, due to the porous nature of the mesh screen and the interstitial deposit of the medicament, turbulent air can completely surround each medicament dose and entrain it, to assure complete dispensing of the medicament dose from the mesh into the air stream.

The turbulence is created in the air flowing through the mesh by passing it through a nozzle and top and bottom pressure plates having alternating smaller and larger diametrical configurations to create pressure changes along the path of the air flow resulting in turbulence of the air as it passes through the mesh to assist in breaking up the compressed dose. Further, the air is first mechanically compressed and then driven in a concentrated burst through the disc to assure delivery of a full dose.

The device is always armed before firing and cannot be armed twice before firing thus assuring dispensing one metered dose at a time. In one embodiment of the invention, arming takes place by retracting a finger pull manually extending downwardly from the bottom of the inhalator housing. The finger pull is connected to a U-shaped linkage having a reciprocating piston extending through the bight of the linkage into a cylinder or pressure chamber having an upright nozzle at one end in communication with an impregnated portion of the screen mesh disc and the holes in the pressure plate provided within the housing. A flat spring between the housing and top pressure plate maintains the parts in operative position. When the piston is pulled back in the pressure chamber or cylinder by the finger pull it compresses a drive spring. This motion concurrently pulls each leg of the U-shaped linkage into 180° alignment, thereby locking the retracted alignment of the drive spring, piston and pressure chamber, due to the linear alignment of the leg segments of the linkage. As the linkage is retracted, an advance mechanism causes the impregnated mesh ring to rotate forward by one dose. The advance mechanism can consist of a ring on the inner diameter of the mesh disc having ratchet teeth spaced about the circumference of the ring in contact with a pivotable pawl member connected to the finger pull. Upon retraction of the pull, the pawl member contacts a tooth on the ring to rotate it a distance to cause rotation of a compressed dose in the mesh to a position in communication with the nozzle and an opening in the upper pressure plate. The device is now armed, indexed and ready to fire.

Firing takes place by the user inserting a mouthpiece on the housing into the mount and inhaling orally. This causes a chamber in the housing under a diaphragm to evacuate, thereby pulling the diaphragm down onto a knock out lever pivotally connected to the top of the pivotal connection between the leg segments of the U-shaped linkage. The lever magnifies the downward force of the diaphragm and delivers a component of the force to the joint of the legs of the linkage, moving this point out of its 180° alignment, to break the linear linkage leg alignment. At this point the structural strength of the linkage is greatly reduced and overpowered by the force of the compressed drive spring. The piston is thus forced into the pressure chamber at high velocity. The volume in the pressure chamber is then compressed to the point where the stroke of the piston hits a pin, opening a spring-backed valve. At this point the reduced volume at high pressure is forced up through the nozzle and through successive layers of the pressure plates and impregnated disc. When the burst of air hits the impregnated disc, the dose is forced out of the mesh's interstices, producing a cloud of the drug in its powdered form. Immediately following the pressurized burst, a vent is opened, allowing make-up air to be pulled up behind the burst of powder assisting inhalation of the drug through the mouthpiece. This completes the firing phase and the device is ready for rearming.

In a second embodiment of the invention, the inhalator is armed by rotating the lower half of a casing 90° in a clockwise direction. The casing has an upper half threadedly or otherwise rotatably mounted on the lower half. A flat cam has a portion of its circumference seated on a lip of the lower half of the casing and includes an arcuate indentation which is adapted to contact a lug or pin on the rear of a wing-shaped piston mount having a piston projecting forwardly therefrom. Upon rotation of cam in a clockwise direction with lower half of the casing, the indentation will surround the lug and retract the mount and compress a pair of expandable springs. The springs normally urge the piston forward in a cylinder fixedly mounted in a bracket on the lower half of the casing. Upon movement of the piston in the cylinder air in the cylinder will first be compressed until the pressure builds sufficiently to open a valve against the force of a valve spring contained within a housing at the end of cylinder. Once the valve is opened, the compressed air in the cylinder will enter air orifice at the top of the cylinder, and burst through an adjacent screen mesh disc containing discrete doses of a suitable medicament, entraining the medicament upon inhalation inducing suction in an air passageway in the interior of a mouthpiece extending upwardly from upper half of the casing.

The springs impelling the piston mount forward into the cylinder are allowed to act upon the piston mount upon inhalation of the user through a mouthpiece which cause flexure of a diaphragm which in turn rocks or pivots a lever out of contact with a stop enabling the springs to push the piston mount forward.

As with the first embodiment, means are also provided to index and advance the medicament ring to present a discrete dose for firing on top of the cylinder orifice.

BRIEF DESCRIPTION OF THE DRAWINGS

Further objects and advantages of the invention will become apparent from the following description and claims, and from the accompanying drawings, wherein:

FIG. 1 is an exploded perspective of a first embodiment of the inhalator of the present invention;

FIG. 2 is a longitudinal cross-sectional view of the assembled inhalator of FIG. 1 in its armed or ready-to-fire position;

FIG. 3 is a cross sectional view similar to FIG. 2, but illustrating the inhalator after having been fired;

FIG. 4 is a cross-sectional view taken substantially along the plane indicated by line 4—4 of FIG. 2;

FIG. 5 is a top perspective view of a second embodiment of the inhalator of the present invention;

FIG. 6 is a bottom perspective view of the inhalator of FIG. 5;

FIGS. 7A and 7B, when combined, are an exploded perspective view of the inhalator of FIGS. 5 and 6, illustrating the components thereof from top to bottom;

FIG. 8 is an exploded perspective view of the piston and cylinder subassembly used in the inhalator of FIG. 5;

FIG. 9 is an exploded perspective view of a cassette containing a medicament carrying disc which is used with the inhalator of FIG. 5;

FIGS. 10A, 10B, and 10C are longitudinal sectional views of the inhalator of FIG. 5 illustrating a cocked or armed, ready-to-fire position of the inhalator, an interim position of the components of the inhalator upon inhalation by the user, and the fired or spent condition of the inhalator, respectively;

FIGS. 11A, 11B, and 11C are schematic plan views of a portion of the cassette mounted in the inhalator with a cam used to arm the inhalator and move the medicament carrying disc within the cassette illustrated in successive positions during the arming of the inhalator and moving of the medicament carrying disc to position an unused dose on the periphery of the disc in the armed condition of the inhalator; and FIGS. 12A, 12B, and 12C are plan views of the opened, bottom portion of the inhalator of FIG. 5, with the corresponding cam portions illustrated in FIGS. 11A–11C during the arming movement of the inhalator.

DETAILED DESCRIPTION OF THE PREFERRED EMBODIMENT

Referring now to the drawings in detail, wherein like numerals indicate like elements throughout the several views, and specifically the embodiment of the invention illustrated in FIGS. 1 to 4, an inhalator 20 of the present invention utilizes a screen mesh disc 10 which constitutes a medicament carrier. The medicament carrier 10 is of a size to be inserted within the breath-activated dry powder inhalator 20 illustrated in FIGS. 1 and 2, and can be a part of a preassembled cassette 50 comprising upper and lower ring shaped plates 40, 42 sandwiching the mesh 10, a pressure plate 44 and flat spring plate 46, all provided with aligned openings 48 for the dispensing of a predetermined dose of a medicament 16 impregnated at spaced locations around the circumference of mesh disc 10.

The screen mesh disc 10 can be formed from woven or non-woven material, or stamped from a metal blank or even photo acid etched from stainless steel or ceramic to provide a plurality of small interstices. Compressed within the interstices at spaced locations along the circumference of the screen mesh disc 10 is a prescribed dose 16 of a medicament. The size of the dose 16 depends upon the drug used. For example, a common drug used for asthmatics is salmeterol hydronapthoate which is to be dispensed in single doses of approximately 50 micrograms. Each medicament dose 14 of this drug should be approximately 0.120 to 0.125 inches in diameter with a thickness of about 0.002 inches to achieve the prescribed dose.

The screen mesh disc 10 can be formed with interstices of approximately 0.004 inches square and is positioned between a pair of pressure plates consisting of cassette lower plate 42 and upper pressure plate 44, each having an enlarged opening 48 adapted to register with one of the medicament doses 16 upon indexing of the screen mesh disc 10. The plates 42 and 44 along with flat spring 46 and cassette upper plate 40 distribute the pressure about the periphery of the screen mesh disc 10 to maintain the medicament dose 16 in its impregnated position compressed in the screen mesh disc 10 adjacent the periphery 14. Air can then be forced through the pressure plate opening 48 and the encapsulated screen mesh disc 10 to entrain the dose 16 of the powdered medicament, and the air stream with the entrained medicament is then inhaled through a mouthpiece 32 on the housing top 52 of the inhalator 20 by the patient-user. The disc 10 is disclosed in further detail in copending application Ser. No. 08/025,964, filed Mar. 3, 1993, assigned to the same assignee as the present invention, which disclosure is incorporated herein by reference.

Because the powdered medicament is impregnated and compressed into the screen mesh disc 10, which could be woven, such as a silkscreen, or formed from polyamide fibers, or even stamped or etched from a piece of metal or ceramic, the air impinging upon the mesh and the powdered medicament will cause the medicament to break up as it is pressed up against and passed through the mesh infrastructure or interstices between the mesh fibers or their equivalent to aerosol or atomize the same so that the medicament is presented in appropriate particle sizes for maximum benefit when inhaled. Further, due to the porous nature of the mesh screen and the interstitial deposit of the medicament, air can completely surround each medicament dose and entrain it to assure complete dispensing of the medicament dose from the mesh into the air stream.

In use, the screen mesh disc 10 is loosely clamped between pressure plates 42 and 44 with dose 16 indexed between holes 48 in the pressure plates and cassette top 40 in inhalator 20. The inhalator is armed by retracting a finger pull 54 manually extending downwardly through an opening 56 formed in the bottom 58 of the inhalator housing. The finger pull 54 is connected to a U-shaped linkage 60 having a reciprocating piston 62 extending through a hole 64 in the bight 66 of the linkage 60 into a cylinder 68 or pressure chamber having an upright nozzle 70 at one end receiving in communication therewith a downwardly extending bore 72 on the cassette bottom 42. The nozzle 70 and bore 72 are in communication with an impregnated portion 16 of the screen mesh disc 10, through the hole 48 in the cassette bottom 42. The flat spring 46 between the cassette top 40 and top pressure plate 44 maintains the parts in operative position.

The piston 62 has a flange 74 in contact with bight 66 and when the finger pull 54 connected to the bight is pulled back, the piston 62 in the pressure chamber or cylinder 68 compresses a drive coil spring 76 provided between flange 74 and a horizontal post 78 on housing bottom 58. This motion concurrently pulls each pivotable leg portion 80, 82 of the U-shaped linkage 60 into 180° alignment, thereby locking the retracted alignment of the drive spring 76 and piston 62 in pressure chamber or cylinder 68, due to the centered alignment of the leg segments 80, 82 of the linkage 60.

As the linkage is retracted, an advance mechanism causes the impregnated mesh ring 10 to rotate forward by one dose. The advance mechanism can consist of a ring 84, on the inner diameter of the mesh disc 10 having camming or ratchet teeth 86 spaced about the circumference of the ring in contact with a pawl 85 connected by a hinge 87 to an upright member 88 on the bight 66 of U-shaped linkage 60. Upon retraction of the pull 54, the pawl 85 on upright member 88 contacts one of the teeth 86 on the ring 84 to rotate it a distance so that a compressed dose 16 in the mesh 10 is moved into registration with opening in the nozzle 70 and hole 48 in pressure plate 44. As the ring 84 rotates, e.g., in a clockwise manner as viewed in FIG. 4, the pawl 85 pivots about hinge 87 until it clears contact with the tooth 84 and springs back into contact with a succeeding tooth on ring 84. The device is now armed, indexed, and ready to fire, as shown in FIG. 2.

Firing takes place by the user inserting the mouthpiece 32 on the housing top 52 into the mouth and inhaling orally. This causes the chamber 90 in the housing 20 under a flexible diaphragm 92 to be evacuated as indicated by arrows 94 thereby pulling the diaphragm 92 down onto a knock out lever 96 pivotally seated on the top of a mount 98 encasing the cylinder 68 and extending upwardly from the housing bottom 58.

Figure 4:
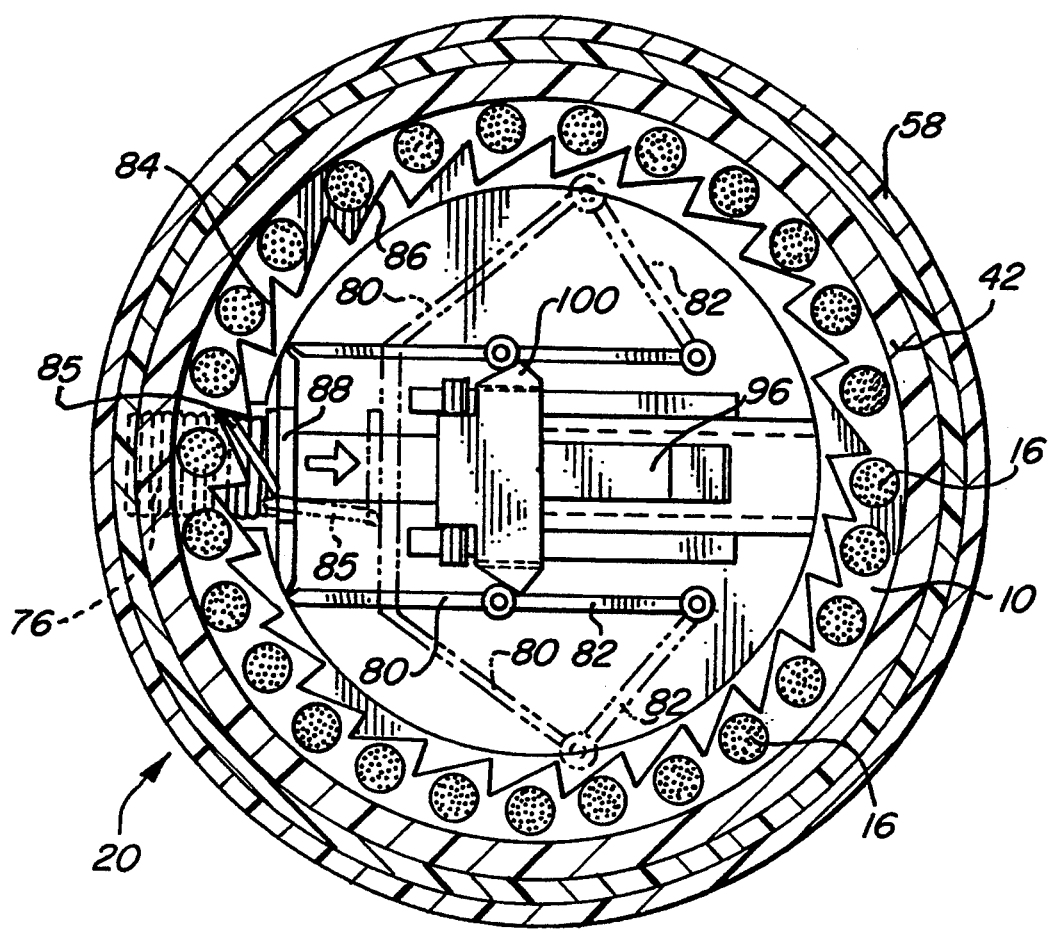
Figure 5:
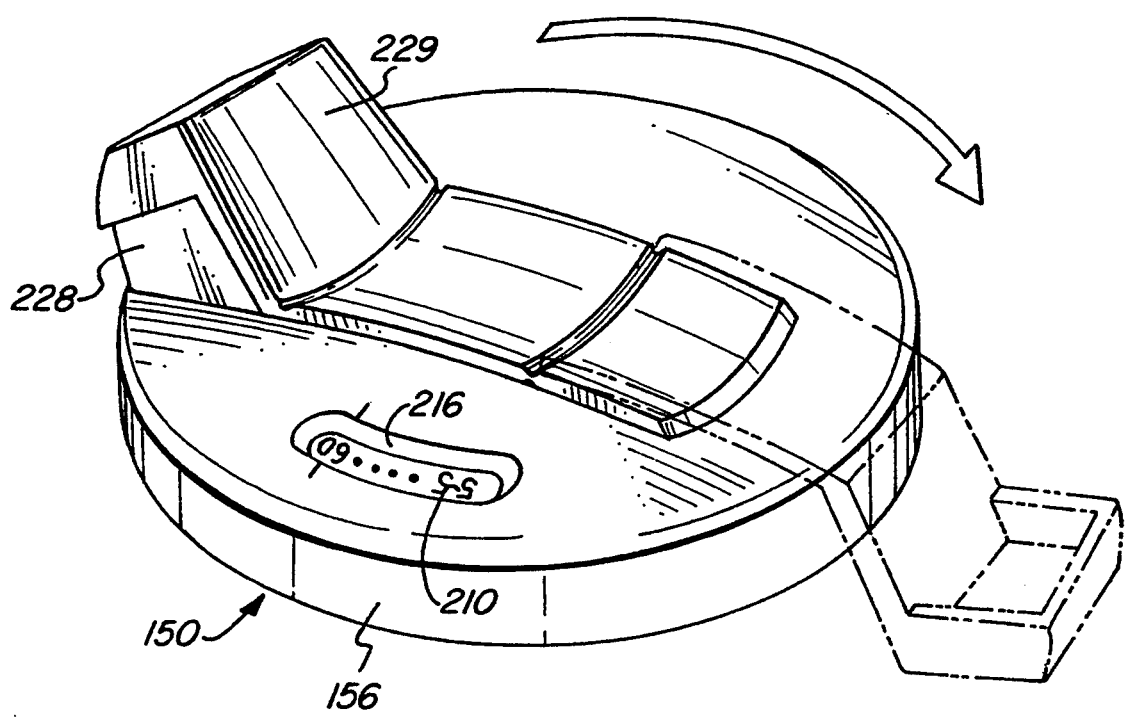

The lever 96 magnifies the downward force of the diaphragm 92 and has tapered legs 100 which straddle the piston 62 adjacent the inner surfaces of legs 80 and 82 of linkage 60 and delivers a component of force to the joint of the legs of the linkage through contact with the joint upon downward movement of the lever, moving this juncture out of its 180° alignment, to break the linear arrangement of the linkage leg alignment, as indicated in FIG. 3 (and in phantom lines in FIG. 4). At this point the structural strength of the linkage 60 is greatly reduced and overpowered by the force of the compressed drive spring 76. The piston is thus forced into the pressure chamber or cylinder 68 at high velocity. The volume of air in the pressure chamber or cylinder 68 is built up and then compressed to the point where the stroke of the piston 62 hits a pin 102 compressing a spring 104 between the head of pin 102 and a plug 106. The head 107 of the pin 102 serves as a valve opening and closing opening 108 between the interior of cylinder 68 and nozzle 70.

At this point, a reduced volume of compressed, high pressure air behind the piston 62 is forced from the cylinder, up through the smaller diameter nozzle and through the larger diameter holes 48 in successive layers of the pressure plates and the impregnated disc 10, in a turbulent burst. When the burst of air hits the impregnated disc 10, the dose 16 is forced out of the mesh's interstices, producing a cloud of the drug in its powdered form.

Immediately following the pressurized burst, the vent 56 is reopened, allowing make-up air to be pulled up behind the burst of powder assisting inhalation of the drug through the mouthpiece, and returning diaphragm 92 to its nonflexed condition of FIG. 2. This completes the firing phase and the device is ready for rearming.

The cartridge 50, when the medicament doses 16 are all spent, may be replaced in its entirety by separating housing top 52 and housing bottom 58 by pulling them apart (a lip 110 on the circumference of top 52 is received in snap seated engagement on a ledge 112 provided adjacent the top of housing bottom 58), and removing and replacing the spent cartridge with bore 72 seated in nozzle 70. A window 114 can be provided in the housing top 52 for viewing of whether the housing has been provided with a cartridge 50, or alternatively, if the pressure plates are transparent, appropriate indicia on disc 10 can be viewed to indicate the number of doses remaining on the disc.

Figure 6:
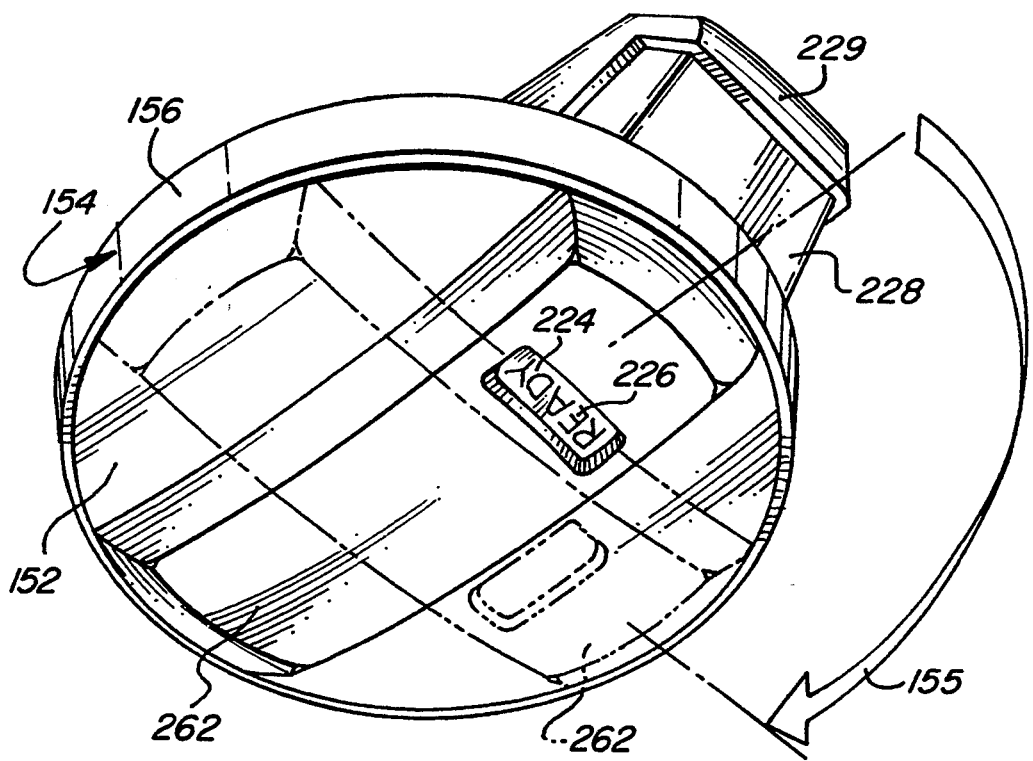
Figure 7A:
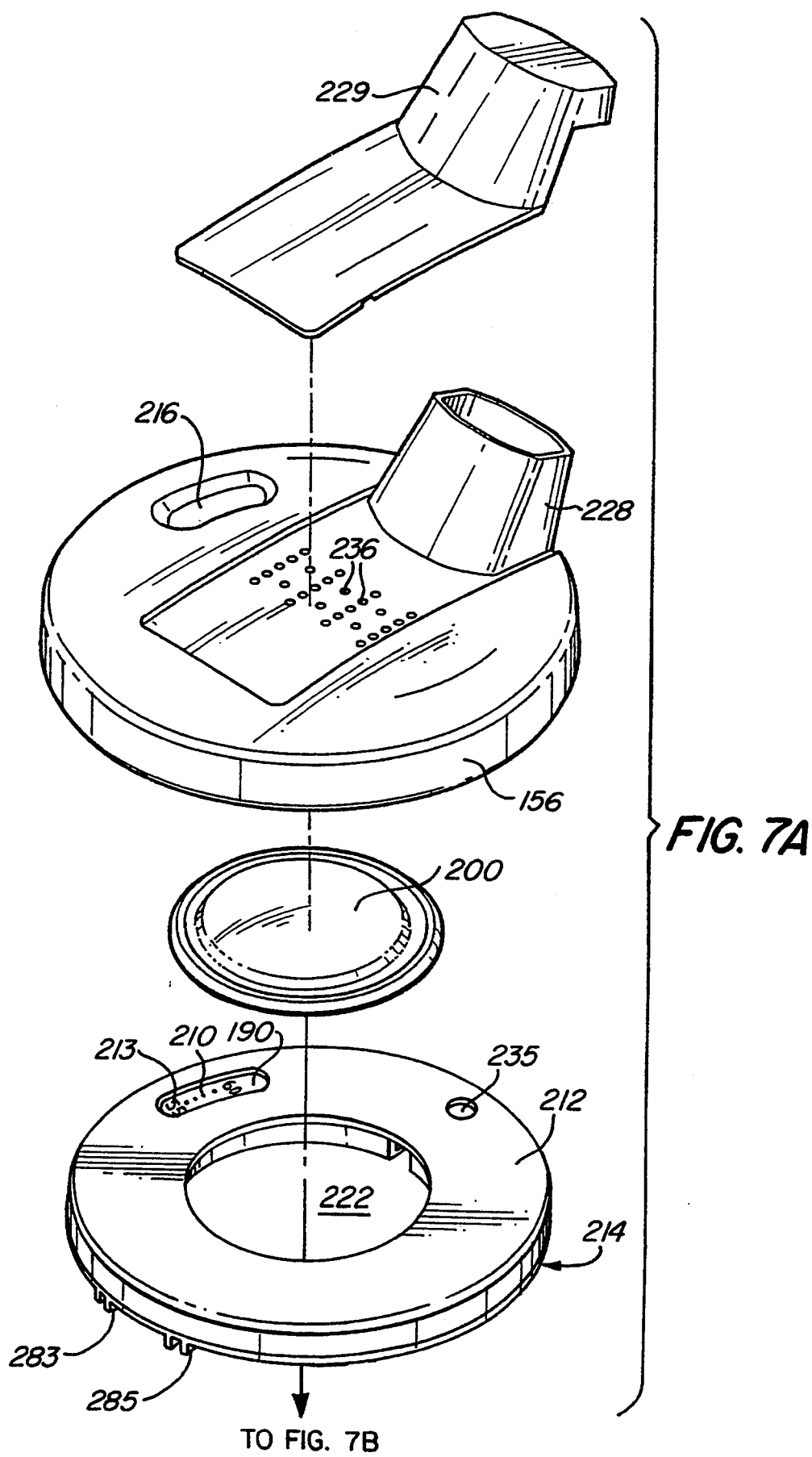
Figure 7B:
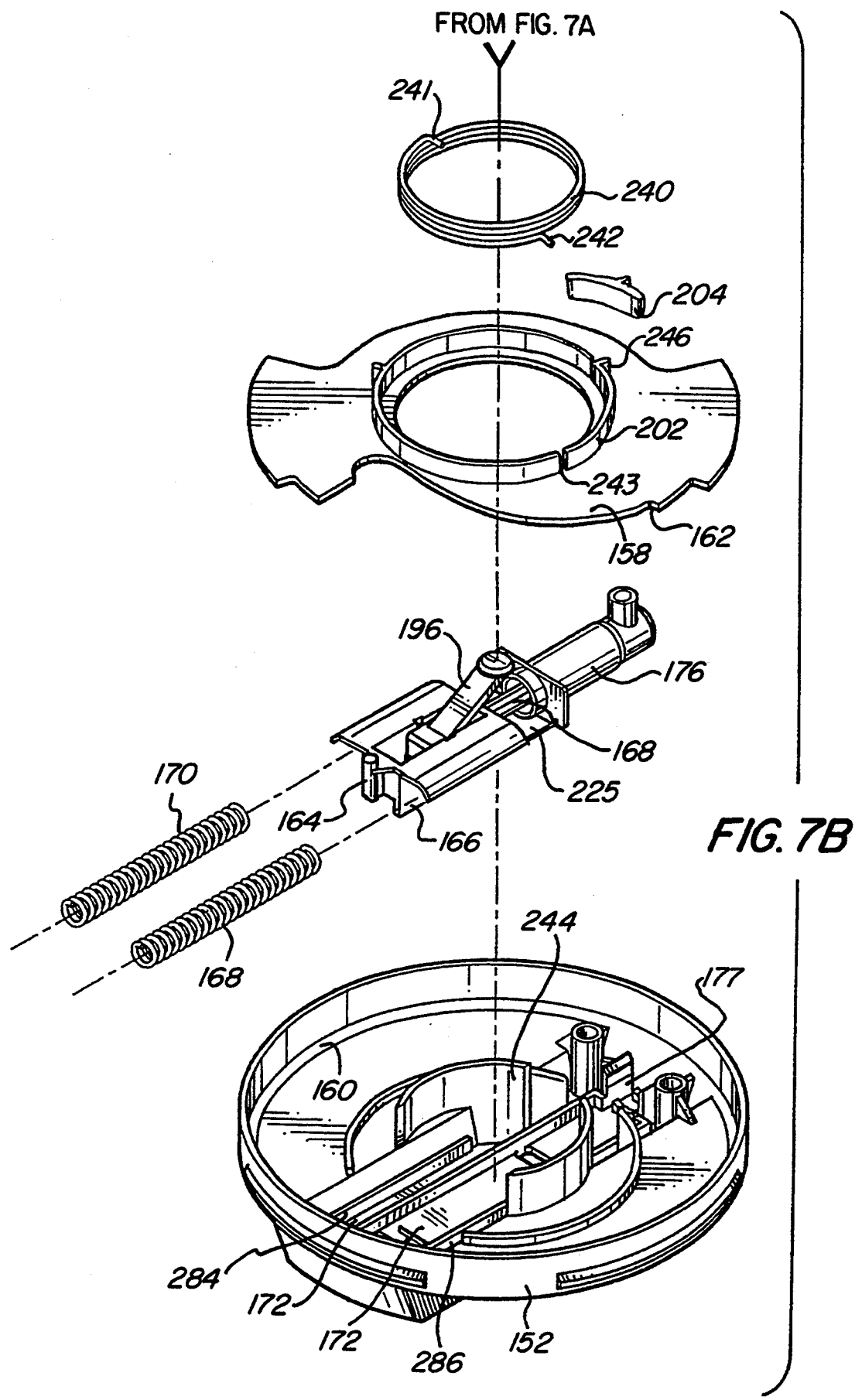
Figure 8:
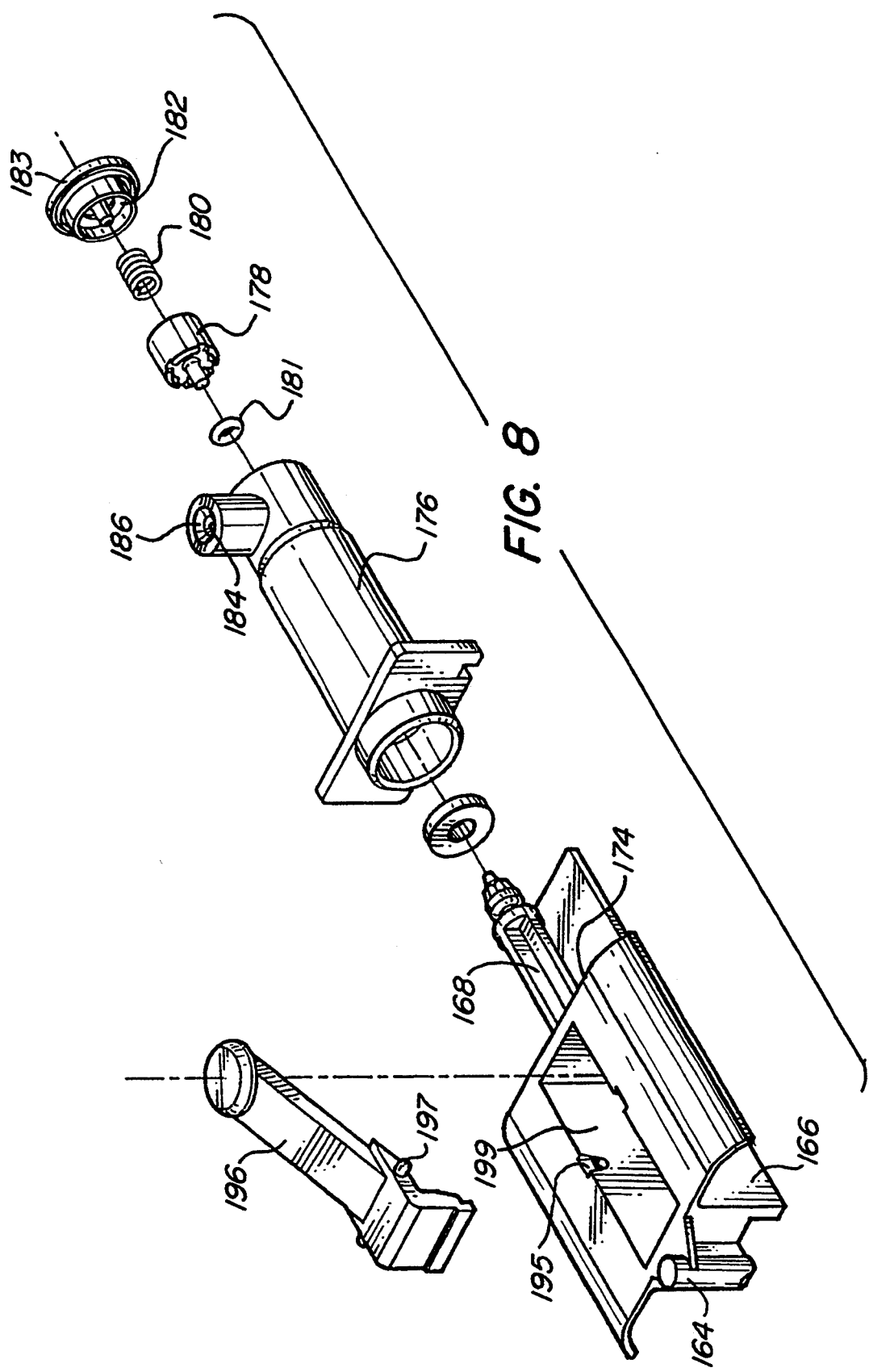
Figure 9:
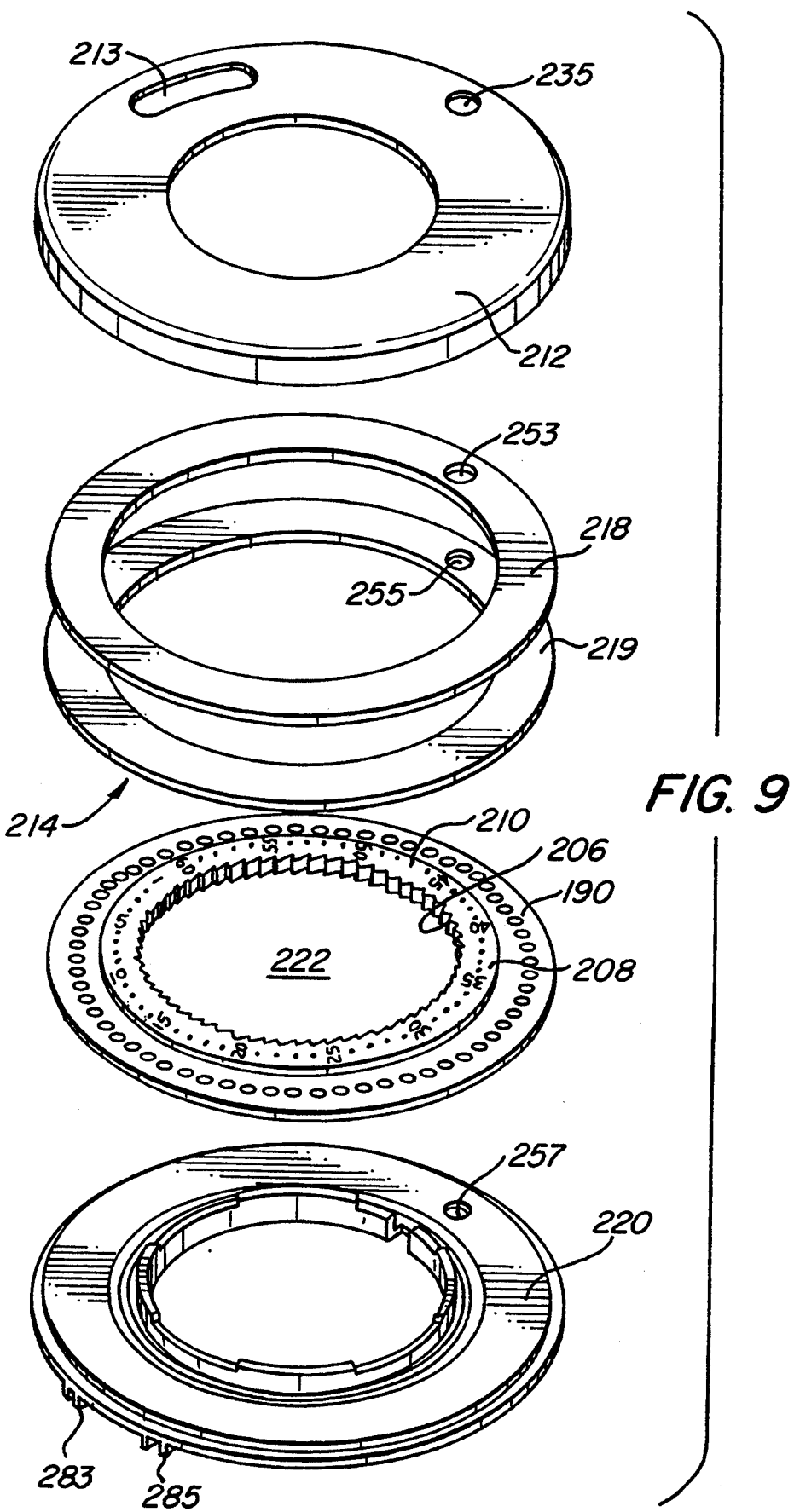

FIGS. 5 to 12C illustrate a second embodiment of the invention, wherein an inhalator 150 is armed by grasping a handle 262 and rotating the lower half 152 of a casing 154 90° in a clockwise direction as indicated by the bottom arrow 155 to the phantom line position illustrated in FIG. 6. The casing has an upper half 156 threadedly or otherwise rotatably mounted on the lower half 152. A flat cam 158 has a portion of its circumference seated on a lip 160 of the lower half 152 of casing 154 and includes an arcuate indentation 162 which is adapted to contact a lug or pin 164 on the rear of a wing-shaped piston mount 166 having a piston 168 projecting forwardly therefrom. Upon rotation of cam 158 in a clockwise direction with lower half 152 of casing 154, indentation 162 will surround lug 164 and cause the piston mount 166 to move to the left in the sequence illustrated in FIGS. 12A and 12B, to retract the mount 166 and compress a pair of expandable coil springs 168, 170 housed in grooves 172 on the bottom of the lower half 152 of casing 154. The springs 168, 170 which impinge upon a rear surface 174 of piston mount 166 normally urge the piston 168 forward in a cylinder 176 fixedly mounted in a bracket 177 on the lower half 152 of casing 154. Upon movement of the piston 168 in cylinder 176 air in the cylinder will first be compressed until the pressure builds sufficiently to open a valve 178 against the force of a valve spring 180 contained within a housing 182 formed in a plug 183 at the end of cylinder 176. An O-ring seal 181 normally seals the interior of cylinder 176 from an orifice 184 at the top of cylinder 176. Once valve 178 is moved to the right and opened, (see FIG. 10C) the compressed air in cylinder 176 will enter orifice 184 in the top of cylinder 176. The orifice 184 is expanded or flared outwardly at 186 so the air initially compressed by the piston 168 in cylinder 176 at high pressure and low volume will expand and burst through an adjacent screen mesh disc 190 containing discrete doses 192 of a suitable medicament, entraining the medicament upon inhalation inducing suction in air passageway 194 in the interior of a mouthpiece 228 extending upwardly from upper half 156 of casing 154.

Figure 10A:
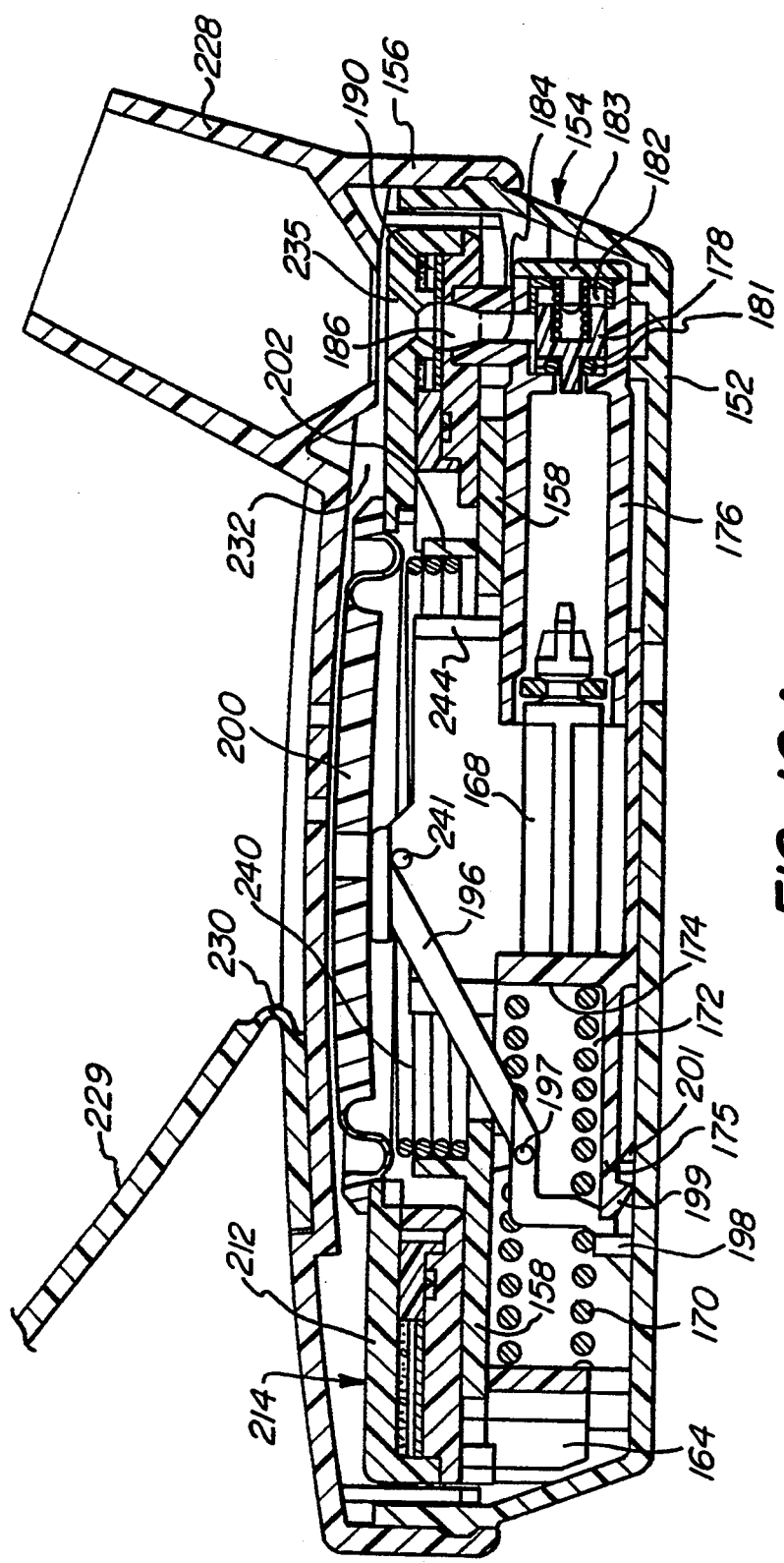
Figure 10B:
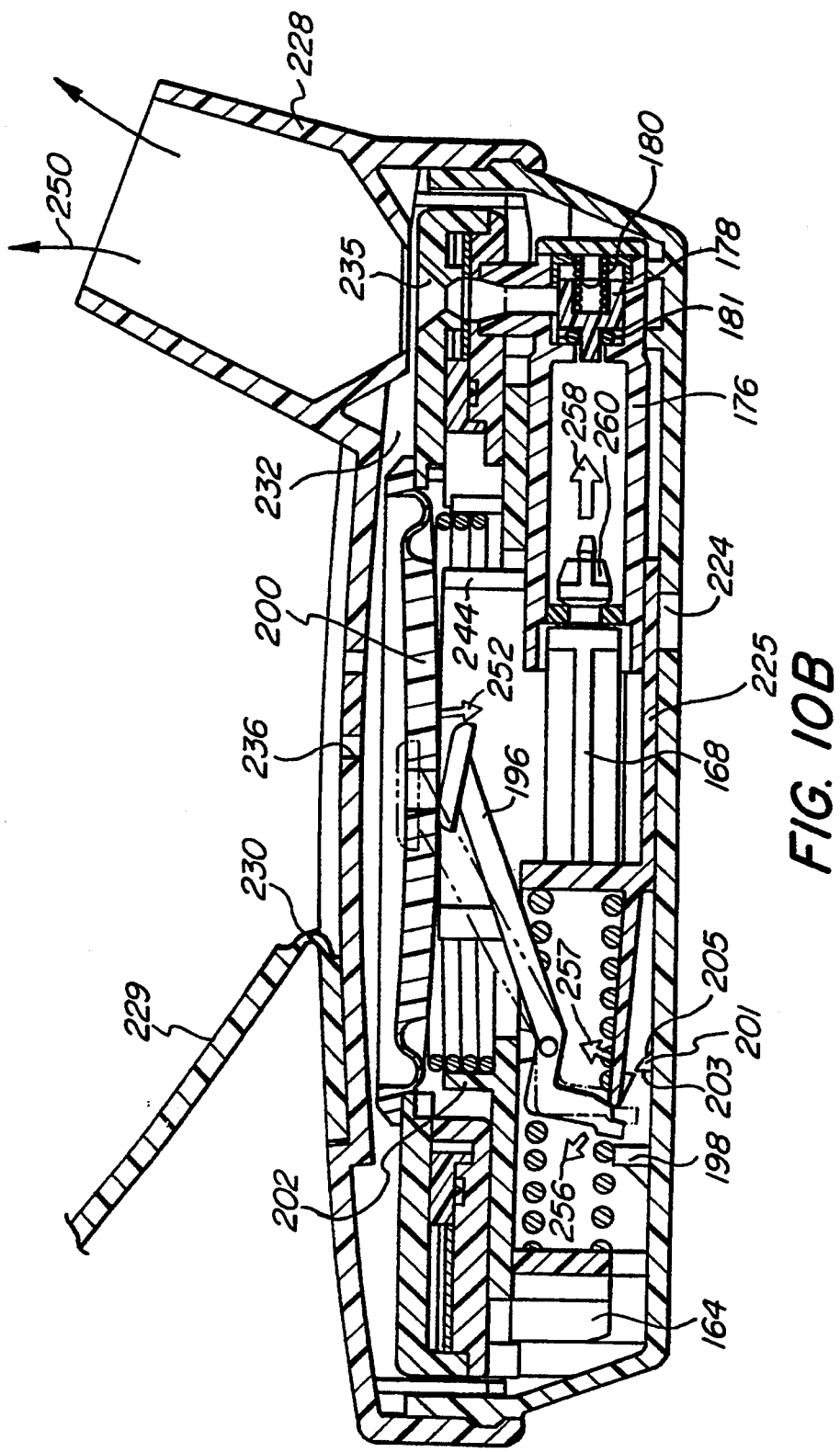
Figure 10C:
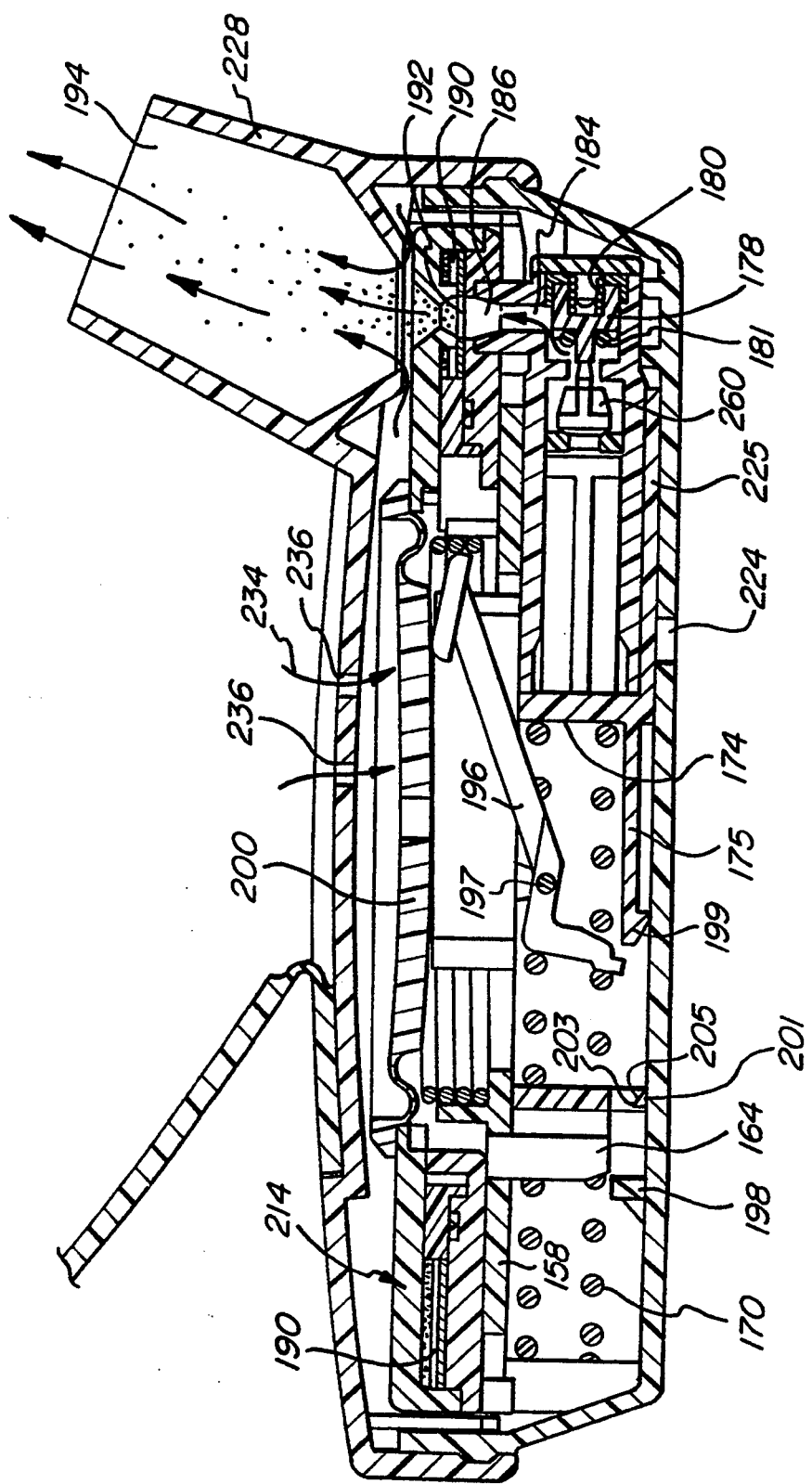

Cam 158, during arming of the inhalator 150, carries the pin or lug 164 to the left as viewed in FIGS. 10A, 10B and 10C, along with the piston mount 166. The rear surface 174 of piston mount 166 includes a linear extension 175 which, during arming of the inhalator 150, will move rearwardly during compression of springs 168, 170, along with a lever 196 pivotably mounted by pins 197 between interior sidewalls 199 of piston mount 166, in slots 195. The rear of lever 196 will ride over an inclined surface 205 of a detent 201 and abut a stop 198 to limit further travel of the piston mount 166 and will cause the lever to pivot in a counterclockwise direction about pins 197. The springs will then tend to push mount 166 forward (from its position in FIG. 10A), but hook 199 will engage behind upright detent 201 having opposed angled or bevelled surfaces 203, 205 extending upwardly from the bottom surface of lower half 152 of casing 154. Upon riding over detent 201, an audible click can be heard indicating that the inhalator has been armed.

Figure 11A:
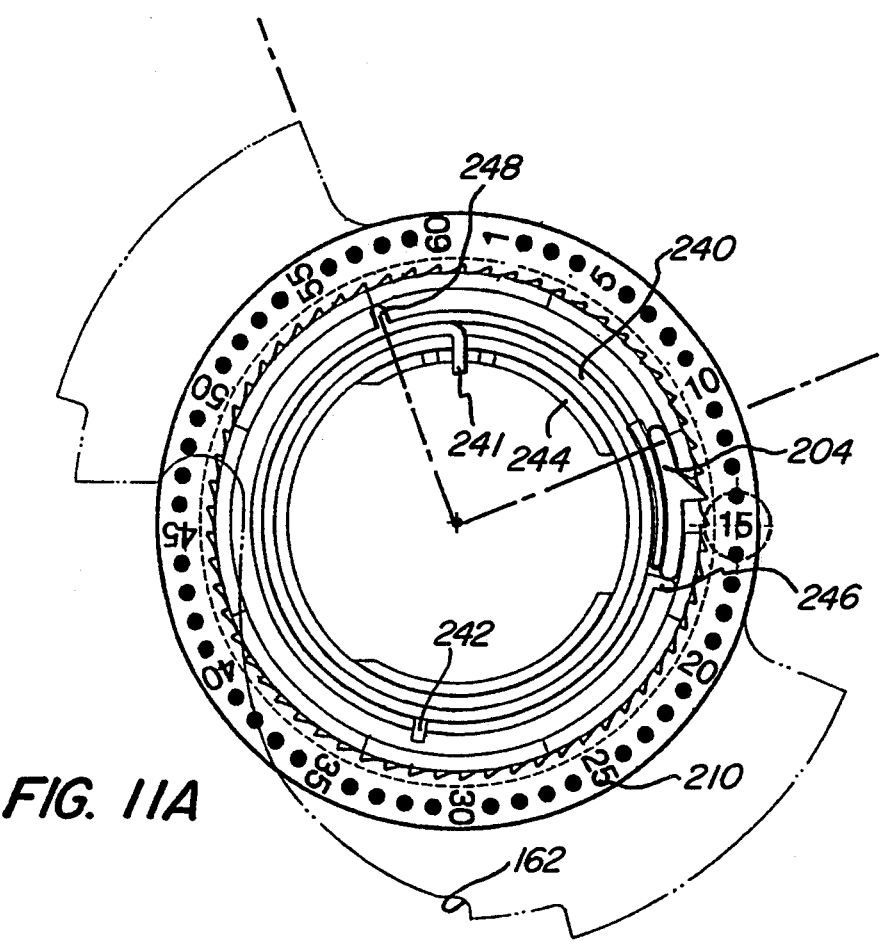
Figure 11B:
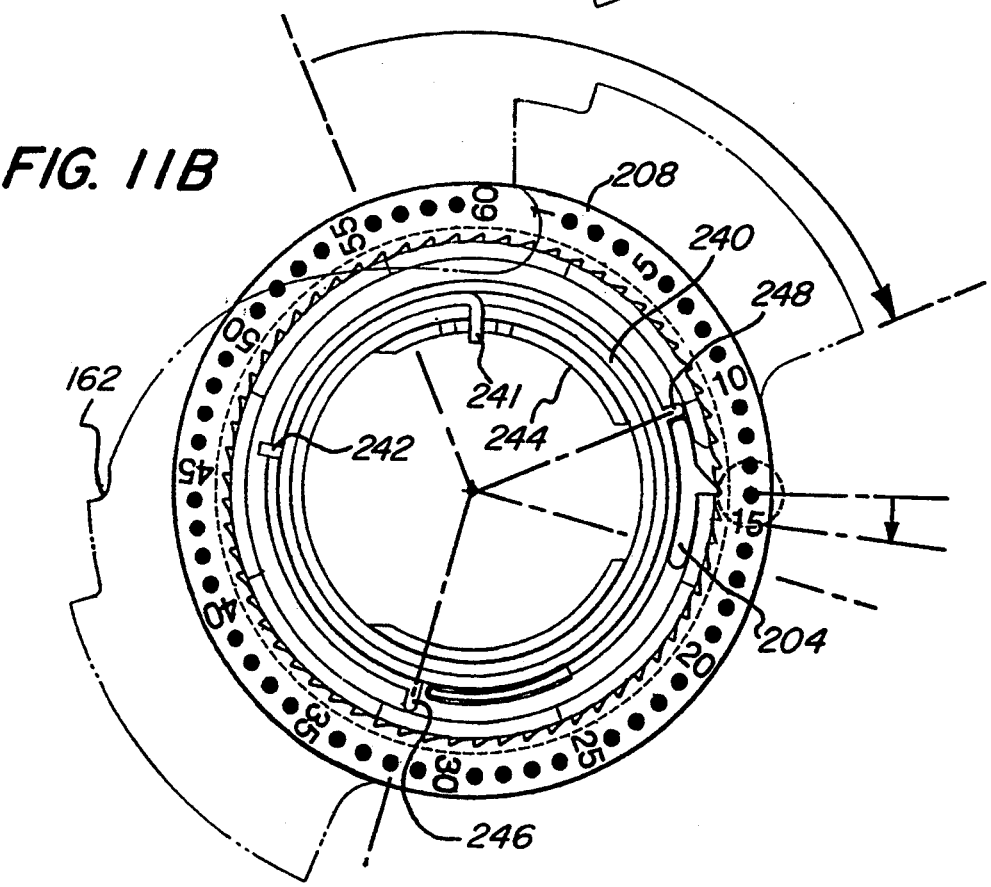
Figure 11C:
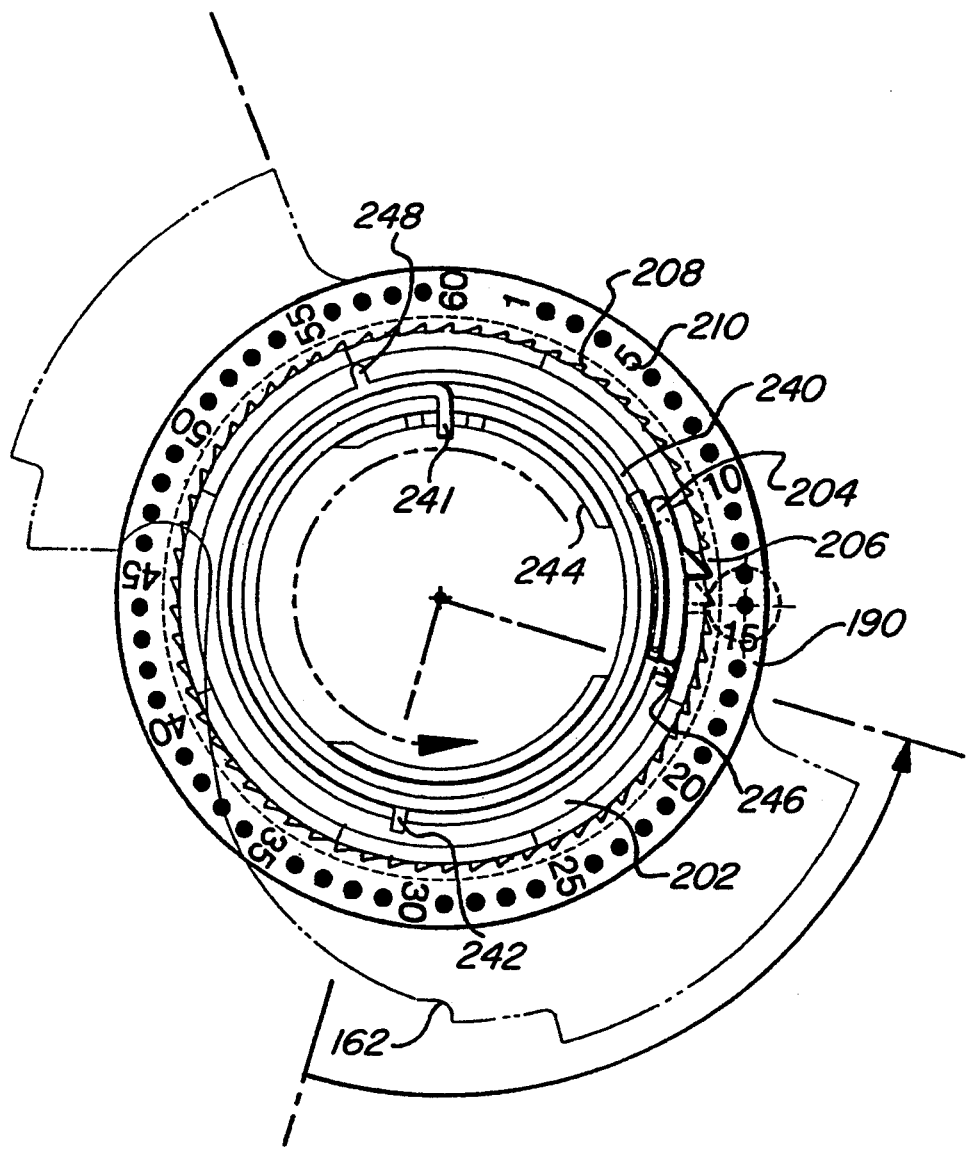
Figure 12A:
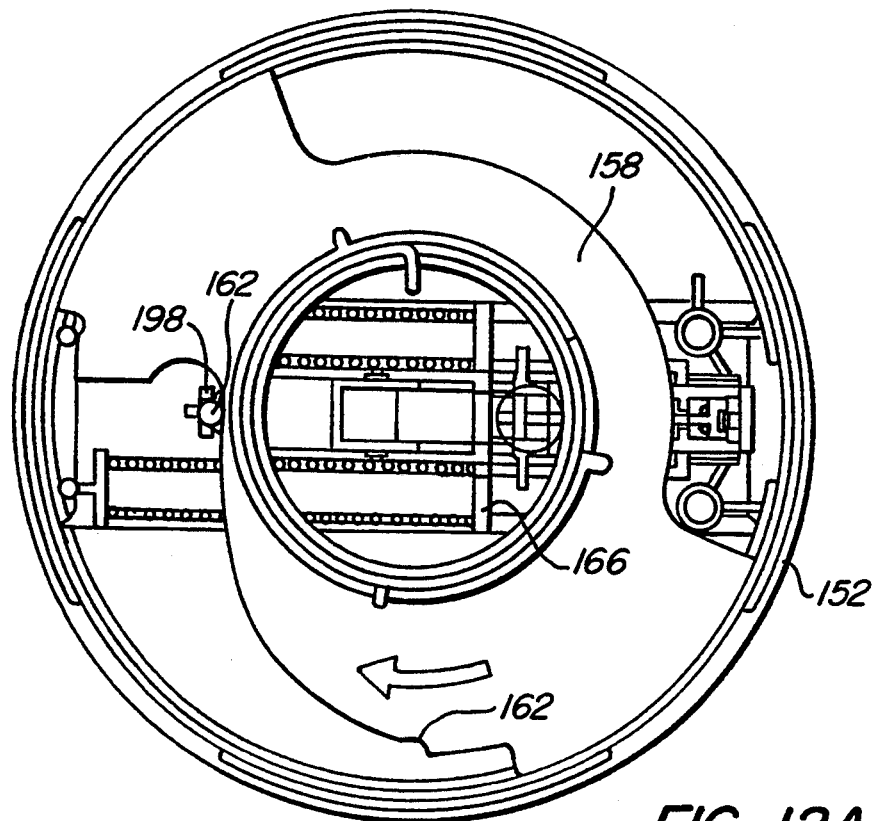
Figure 12B:
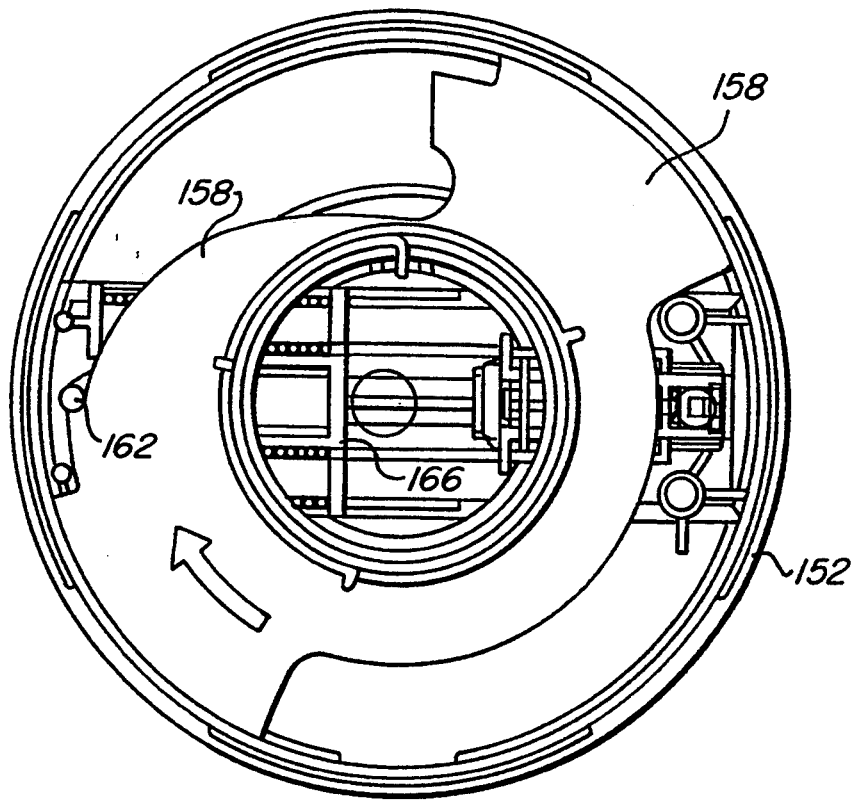
Figure 12C:
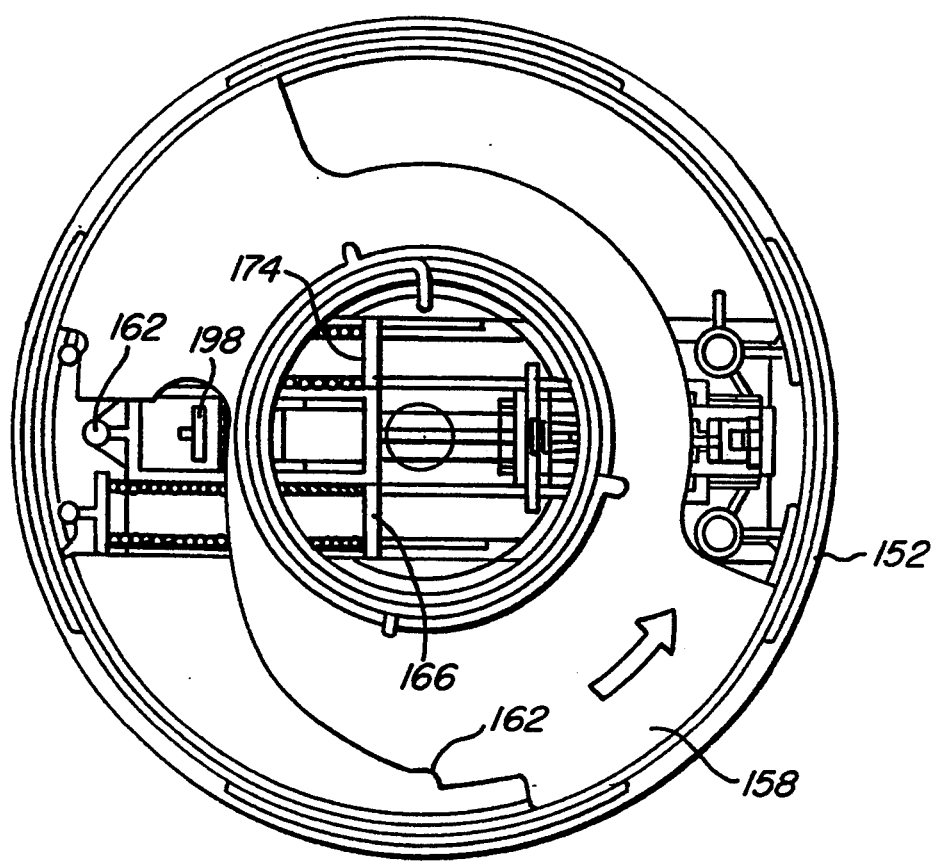

Upon pivoting the lever 196 in a counterclockwise direction, it will contact the lower surface of a flexible diaphragm 200 seated along its circumference on top of a unitary cassette 214 within casing 154 and cause the center of the diaphragm to expand from a concave fired condition (FIGS. 10B, 10C) to a convex armed condition (FIG. 10A). A torsion spring 240 having an end 242 disposed in a slot 243 on a split ring hub 202 on cam 158 and its other end 241 inserted in a concentric hub 244 on casing lower half 152 will cause the cam 158 to return 90° to its precocked position in a counterclockwise direction as indicated by the top of arrow 155 and as illustrated in FIGS. 11B and 11C (and 12B and 12C). A pawl 204 seated on and freely movable along the upper surface of cam 158 between radial nubs 246, 248, extending outwardly from split ring hub 202 on cam 158 is contacted by and slightly rotated (see FIGS. 11B and 11C) first by nub 248 and then nub 246 upon return of cam 158. One of the ratchet teeth 206 on a ring disc 208 affixed to the inner surface of the mesh medicament carrying disc 190, is engaged by pawl 204 and advances the disc 190 one dose upon movement of the pawl on cocking inhalator 150 to position the same over the air burst orifice 184. The pawl 204, upon return movement of cam 158 will then be repositioned by nub 246 for engagement with the next adjacent ratchet tooth 206 (see FIG. 11C).

Disc 190 can contain suitable indicia 210 indicating the number of the dose next to be dispensed so a user can determine the amount of the remaining doses on the disc 190. This may be viewed through a transparent cover 212 or opening 213 in the cover on the disc cassette 214 and window 216 on the upper half 152 of casing 154.

The cassette 214 has upper and lower pressure plates 219, 220 along with a spring disc 218 loosely clamping the disc 190 therebetween and a central opening 222 permitting access to the ring disc 208. The cover includes a dispensing opening 235 adapted to be aligned with openings 253, 255 and 257 in the spring disc 218, and pressure plates 219, 220 and one of the doses on disc 190 as it is brought into registration between the openings. The bottom 220 of cassette 214 includes parallel tracks 283, 285 for mounting the cassette on bars 284, 286 respectively, provided in the interior of bottom 152 of casing 154. In this manner, the cassette 214 can be replaced as a unit in the interior of inhalator 150.

The lower half 152 of casing 154 also includes a window or opening 224 which can be used to view indicia 226, comprising the word "READY" on the bottom of the cocked inhalator, which is imprinted on the bottom of a forwardly extending flat slide 225 of piston mount 166. The slide 225 extends forwardly from the wall 174.

The upper half 156 of casing 154 also includes a mouthpiece 228 having a cover 229 which is pivotably connected to the upper half of casing 156 by a living hinge 230. Mouthpiece 228 opens into the chamber 232 surrounding cassette 214 in the interior of the inhalator 150 and is in communication with orifice 184 through the opening 235 in the cassette cover 212, along with openings 253, 255 and 257 in the cassette components. Make-up air, as indicated by arrows 234 can be drawn from the exterior of upper half 152 of casing 154 through openings 236 to aid in entraining the medicament leaving disc 190.

The sequence involved in firing of the inhalator 150 upon inhalation of the medicament is illustrated in FIGS. 10A–10C, inclusive. With the inhalator 150 cocked and ready to fire as described hereinbefore, the components of the device appear as in FIG. 10A. To use, the patient pivots cover 229 about hinge 230 to expose the mouthpiece 228. As illustrated in FIG. 10B, upon the user or patient inhaling air through the mouthpiece 228 as illustrated by the arrows 250, air is evacuated from chamber 232 causing air to enter through the openings 236. The combination of positive pressure on one side of the diaphragm 200 due to the air impinging thereon from openings 236 in conjunction with the negative pressure beneath the diaphragm caused by the evacuation of chamber 232 causes the diaphragm to flex from its convex condition illustrated in FIG. 10A to a concave condition as illustrated in FIG. 10B. The diaphragm 200 will move downwardly as indicated by the arrow 252 and hit the top of the lever 196 pivoting it about pivot pins 197 from the phantom to full position illustrated in FIG. 10B or in a clockwise direction. The distal end of the lever 196 will rotate and clear the stop 198 as indicated by arrow 256. The force of springs 168 and 170 will then cause the linear extension 175 of rear surface 174 of the piston mount 166 to move forwardly and hook 199 will ride upwardly as indicated by the arrow. 257 over inclined surface 203 of detent 201 until the hook 199 clears the stop detent 201. When this occurs, compressed coil springs 168 and 170 move the piston mount 166 and piston 168 further to the right as illustrated in FIGS. 10B in cylinder 176. Air within the interior of the cylinder 176 is compressed. This is indicated by the arrow 258 in FIG. 10B. At its forward end the head of the piston 260 compresses the air within cylinder 176 until the force of spring 180 is overcome and valve 178 is opened as indicated in FIG. 10C. The piston 260 comes to rest against the valve 178. The air compressed within cylinder 176 can then escape through port 184 and is dispensed in a burst of high pressure, low volume through medicament 192 on screen mesh disc 190, which is dispensed into the passageway 194 in mouthpiece 228. Make-up air 234 can also be entrained with the medicament in the passageway 194 in mouthpiece 228 to aid in inhalation.

By rotating the downwardly extending handle 262 in a clockwise direction as in FIG. 6 to the phantom position illustrated, it will recock or reset the components as previously described to the condition illustrated in FIG. 10A. Cam 158 will cause axial displacement of the piston mount to the left as viewed in FIG. 10C as shown specifically in FIGS. 12A–12C, inclusive, and the medicament disc advanced as illustrated in FIGS. 11A–11C, inclusive. Torsion spring 240 will return the handle and lower half of casing 154 to its original position as illustrated in FIG. 6 wherein the slide 225 has been repositioned so that the word or indicia "READY" 226 appears in the window 224.

What is claimed is:

1. A dry powder breath-activated inhalator apparatus comprising
   a housing,
   a disc having at least one screen mesh portion in said housing, at least one predetermined dose of a powdered medicament embedded in said screen mesh portion of the disc for entrainment with a flow of air introduced through said mesh,
   a mouthpiece on said housing in communication with said dose of medicament impregnated in said screen mesh for evacuating air from the interior of said housing and providing a means for ingesting said medicament dose,
   means in said housing for first compressing air and then dispensing said air in a concentrated burst through said screen mesh and dose in response to evacuation of air from said housing through said mouthpiece,
   said compressing and dispensing means including
   a cylindrical chamber filled with air,
   a piston in said chamber adapted to be reciprocated within said chamber to compress the air in said chamber,
   a nozzle on one end of said cylindrical chamber in alignment with said impregnated dose in said screen mesh and mouthpiece,
   means in said chamber for establishing communication between said chamber and nozzle only after a predetermined pressure of compressed air has been reached in said chamber,
   means in said housing for arming said piston to drive said air from said chamber through said nozzle and dose in said mesh screen to said mouthpiece,
   means in said housing for moving said piston from said armed position to a fired position in response to evacuation of air from said housing through said mouthpiece,
   said arming means including
   a U-shaped linkage having a bight and a pair of pivotably connected legs extending from opposite ends of said bight straddling said piston,
   said piston extending through said bight,
   spring means between said housing and bight of said linkage for driving said piston forward in said cylindrical chamber, and
   a finger pull connected to said bight for compressing said spring means and locking said piston in a retracted position in said cylindrical chamber by maintaining said pivotably connected legs of said linkage in 180° alignment.

2. The inhalator of claim 1 wherein said means for moving said piston from said armed to said fired position includes
   flexible diaphragm means in said housing adapted to move in response to the withdrawal of air from the interior of said housing,
   a knock-out lever in the path of movement of said flexible diaphragm means for contact with each pair of said pivotably connected legs of said linkage upon flexure of said diaphragm means to pivot and break the 180° alignment of said legs and lock on said piston,
   whereby said piston can move forward in said cylindrical chamber to discharge a burst of air through said nozzle.

3. The inhalator of claim 2, wherein said disc includes a plurality of doses of powdered medicament spaced around its periphery and means are provided in said housing for rotating said disc upon arming said inhalator to serially present individual ones of said doses into alignment with said nozzle.

4. The inhalator of claim 3 wherein said disc rotation means includes
   a ring on said disc having a plurality of ratchet teeth around the inner circumference thereof, and
   means on said bight of said linkage in contact with said teeth for imparting a predetermined amount of movement to said teeth and ring in response to movement of said finger pull to compress said spring means and lock said piston in its retracted position.

5. The inhalator of claim 6, wherein said disc includes a plurality of doses of powdered medicament spaced around its periphery and means are provided in said housing for rotating said disc upon arming said inhalator to serially present individual ones of said doses into alignment with said nozzle.

6. A dry powder breath-activated inhalator apparatus comprising
   a housing,
   a disc having at least one screen mesh portion in said housing, at least one predetermined dose of a powdered medicament embedded in said screen mesh portion of the disc for entrainment with a flow of air introduced through said mesh,
   a mouthpiece on said housing in communication with said dose of medicament impregnated in said screen mesh for evacuating air from the interior of said housing and providing a means for ingesting said medicament dose,
   means in said housing for first compressing air and then dispensing said air in a concentrated burst through said screen mesh and dose in response to evacuation of air from said housing through said mouthpiece,
   said compressing and dispensing means including
   a cylindrical chamber filled with air,
   a piston in said chamber adapted to be reciprocated within said chamber to compress the air in said chamber,
   a nozzle on one end of said cylindrical chamber in alignment with said impregnated dose in said screen mesh and mouthpiece, means in said chamber for establishing communication between said chamber and nozzle only after a predetermined pressure of compressed air has been reached in said chamber, means in said housing for arming said piston to drive said air from said chamber through said nozzle and dose in said mesh screen to said mouthpiece, means in said housing for moving said piston from said armed position to a fired position in response to evacuation of air from said housing through said mouthpiece, said housing having two portions relatively rotatable with respect to the other said arming means including a mount in said housing having a piston extending therefrom, spring means between said housing and mount for driving said mount and piston forward in said cylindrical chamber, and cam means in one of said relatively rotatable housing portions between said housing portion and piston mount for linearly retracting said mount against the force of said spring means in response to rotation of said cam means.

7. The inhalator of claim 6 wherein said cam means is connected to said relatively rotatable housing portion by a torsion spring for returning said cam to its initial position after rotation to arm said inhalator.

8. The inhalator of claim 7 wherein said means for moving said piston from said armed to said fired position includes flexible diaphragm means in said housing adapted to move in response to the withdrawal of air from the interior of said housing, a pivotably mounted knock-out lever in the path of movement of said flexible diaphragm means for holding said piston mount against movement by said spring means in its armed condition and releasing said piston mount in response to pivotable movement of said knock-out lever by contact with said flexible diaphragm means upon withdrawal of air from the interior of said housing, whereby said piston can move forward in said cylindrical chamber to discharge a burst of air through said nozzle.

9. The inhalator of claim 8, wherein said disc includes a plurality of doses of powdered medicament spaced around its periphery and means are provided in said housing for rotating said disc upon arming said inhalator to serially present individual ones of said doses into alignment with said nozzle.

10. The inhalator of claim 9 wherein said disc rotation means includes a ring on said disc having a plurality of ratchet teeth around the inner circumference thereof, and pawl means on said cam means for imparting a predetermined amount of movement to said teeth and ring in response to rotation of said cam means to arm said inhalator.

* * * * *

UNITED STATES PATENT AND TRADEMARK OFFICE
CERTIFICATE OF CORRECTION

PATENT NO. : 5,388,572
DATED : February 14, 1995
INVENTOR(S) : Mulhauser et al.

It is certified that error appears in the above-identified patent and that said Letters Patent is hereby corrected as shown below:

Column 12, In Claim 5, line 1, renumber this claim as --6.-- and change the dependency from "6" to --5--.

Column 12, In Claim 6, line 1, renumber this claim as --5.--.

Column 14, In Claim 7, line 1, change "6" to --5--.

Signed and Sealed this

Fifteenth Day of August, 1995

Attest:

BRUCE LEHMAN

Attesting Officer

Commissioner of Patents and Trademarks